United States Patent [19]
Simroth et al.

[11] Patent Number: 5,955,534
[45] Date of Patent: Sep. 21, 1999

[54] PROCESS FOR THE PREPARATION OF POLYMER POLYOL DISPERSIONS

[75] Inventors: Donald W. Simroth, Charleston, W. Va.; Xinhua Zhou, West Chester; Charles V. Rose, Newtown Square, both of Pa.

[73] Assignee: ARCO Chemical Technology, L.P., Greenville, Del.

[21] Appl. No.: 08/915,101

[22] Filed: Aug. 20, 1997

Related U.S. Application Data

[62] Division of application No. 08/565,516, Nov. 30, 1995, Pat. No. 5,688,861.

[51] Int. Cl.⁶ .............................. C08K 5/06; C08K 5/053
[52] U.S. Cl. ..................... 524/762; 521/137; 524/500; 524/502; 525/123; 525/452; 525/453; 525/457; 525/458
[58] Field of Search ................... 524/762, 500, 524/502; 521/137; 525/123, 452, 453, 457, 458

[56] References Cited

U.S. PATENT DOCUMENTS

| | | | |
|---|---|---|---|
| 3,427,256 | 2/1969 | Milgrom | 552/431 |
| 3,427,334 | 2/1969 | Belner | 556/31 |
| 3,427,335 | 2/1969 | Herold | 549/206 |
| 3,829,505 | 8/1974 | Herold | 568/606 |
| 3,941,849 | 3/1976 | Herold | 528/92 |
| 4,089,835 | 5/1978 | Konig et al. | 524/762 |
| 4,093,569 | 6/1978 | Reischl et al. | 524/762 |
| 4,242,490 | 12/1980 | Emerson et al. | 528/77 |
| 4,296,213 | 10/1981 | Cuscurida et al. | 521/166 |
| 4,305,857 | 12/1981 | Reischl | 524/762 |
| 4,305,858 | 12/1981 | Reischl | 524/762 |
| 4,355,188 | 10/1982 | Herold et al. | 568/620 |
| 4,359,541 | 11/1982 | Patton, Jr. et al. | 521/137 |
| 4,374,209 | 2/1983 | Rowlands | 524/762 |
| 4,386,167 | 5/1983 | Patton, Jr. et al. | 521/161 |
| 4,452,923 | 6/1984 | Carroll et al. | 524/762 |
| 4,472,560 | 9/1984 | Kuyper et al. | 526/120 |
| 4,477,589 | 10/1984 | van der Hulst et al. | 502/169 |
| 4,652,589 | 3/1987 | Simroth et al. | 521/137 |
| 4,721,818 | 1/1988 | Harper et al. | 568/120 |
| 4,837,246 | 6/1989 | Gastinger et al. | 521/137 |
| 4,837,247 | 6/1989 | Gastinger et al. | 521/137 |
| 4,847,320 | 7/1989 | Lowery et al. | 524/762 |
| 4,855,352 | 8/1989 | Lowery et al. | 524/762 |
| 4,985,491 | 1/1991 | Reisch | 524/875 |
| 4,987,271 | 1/1991 | Watabe et al. | 568/621 |
| 5,010,047 | 4/1991 | Schuchardt | 502/24 |
| 5,068,280 | 11/1991 | Pal et al. | 524/762 |
| 5,093,380 | 3/1992 | Takeyasu et al. | 521/131 |
| 5,100,997 | 3/1992 | Reisch et al. | 528/60 |
| 5,158,922 | 10/1992 | Hinney et al. | 502/175 |
| 5,248,833 | 9/1993 | Hinney et al. | 568/621 |
| 5,300,535 | 4/1994 | Takeyasu et al. | 521/137 |
| 5,359,019 | 10/1994 | Hayes et al. | 526/262 |
| 5,364,906 | 11/1994 | Critchfield et al. | 525/53 |
| 5,488,085 | 1/1996 | Hayes et al. | 525/53 |
| 5,496,894 | 3/1996 | Critchfield et al. | 525/53 |
| 5,688,861 | 11/1997 | Simroth et al. | 524/762 |

FOREIGN PATENT DOCUMENTS

| | | |
|---|---|---|
| 2294319 | 12/1990 | Japan . |
| 6228247 | 8/1994 | Japan . |
| 9300495 | 6/1994 | WIPO . |

OTHER PUBLICATIONS

J.L. Schuchardt and S.D. Harper; "Preparation of High Molecular Weight Polyols Using Double Metal Cyanide Catalysts", 32 nd Annual Polyurethane Technical Marketing Conference; Oct. 1–4, 1989.

M.A. Koshute and H.A. Freitag; "Second Generation PHD Polyol for Automotive Flexible Molding", Polyurethanes World Congress 1987; Sep. 29–Oct 2, 1987.

Telechelic Polymers: Synthesis and Applications, ed. Eric J. Goethals, Ph.D. pp. 211, 227, CRC Press, Inc.; Boca Raton, Florida; 1988.

K.G. Spider and J.J. Lindsey, "PHP Polyols, A New class of PUR raw Materials", Journal of Cellular Plastics, Jan./Feb., 1981; Technomic Publishing Co., Inc.

*Primary Examiner*—Rabon Sergent
*Attorney, Agent, or Firm*—Jonathan L. Schuchardt

[57] ABSTRACT

Polymer polyols and polymer-modified polyols having substantially no transition metal content in the polyol continuous phase may be prepared from encapsulative double metal cyanide complex-catalyzed polyoxy-alkylene polyether base polyols without substantial removal of double metal cyanide complex catalyst residues from the base polyol and subsequent in situ polymerization of one or more polymerizable monomers.

18 Claims, No Drawings

PROCESS FOR THE PREPARATION OF POLYMER POLYOL DISPERSIONS

This is a division of application Ser. No. 08/565,516, filed Nov. 30, 1995 now U.S. Pat. No. 5,688,861.

TECHNICAL FIELD

The present invention pertains to a process for the manufacture of polymer polyols by the in situ polymerization of vinyl monomers and to the manufacture of polymer-modified polyols by the in situ polymerization of polyisocyanates and isocyanate reactive monomers, both types of in situ polymerization conducted in the presence of a polyoxyalkylene polyether base polyol. More particularly, the present invention pertains to an improved process for manufacture of polymer polyols and polymer-modified polyols having substantially no catalyst residues in the continuous polyol phase wherein certain double metal cyanide complex-catalyzed polyoxyalkylene polyether polyols are used as the base polyol, and the in situ polymerization are conducted subsequently without removal of double metal cyanide complex catalyst residues. Polyurethane foams prepared from such polyol polymer dispersions surprisingly require less catalyst concentration than similar foams prepared from dispersions employing conventional polyols as base polyols.

BACKGROUND ART

Polymer polyols, as that term is used herein, refers to polyvinyl polymer dispersions prepared by the in situ polymerization of one or more vinyl monomers in a polyoxyalkylene "base" polyol. Polymer-modified polyols, as that term is used herein, refers to polyoxyalkylene polyether polyols having a dispersed phase of a urea or urethane/urea polymer prepared by the in situ polymerization of a diisocyanate or polyisocyanate with an isocyanate-reactive monomer, preferably an amino-functional monomer such as an alkanolamine, diamine, or the like. The majority of such polymer polyols and polymer-modified polyols are used in the polyurethane field for diverse applications, including cell openers and hardness enhancers for polyurethane foam, and as reinforcing additives for a variety of microcellular and non-cellular polyurethanes.

The manufacture of polymer polyols is by now well known, and may involve batch, semi-batch, and fully continuous processes. In all of these processes, one or more vinyl monomers such as acrylonitrile and styrene are polymerized in situ in one or more base polyols, with or without the presence of an added stabilizer. The amount of monomer (s) fed to the reactor is selected to achieve the desired vinyl polymer solids content in the final polymer polyol product. The solids level may range from as little as 5 weight percent to upwards of 60 weight percent, however, it is most economical to produce polymer polyols at relatively high solids loadings even when a low solids product is desired. If a lower solids content polymer polyol is desired, the solids content may be lowered by dilution of the higher solids polyol with further amounts of the same base polyol or other non-polymer polyol, or by blending with a polymer polyol of lesser solids content. The base polyol functionality is dictated by the particular polyurethane end-use desired, and may typically involve nominal functionalities of two to eight. The details of polymer polyol manufacture will be presented hereafter.

The manufacture of polymer-modified polyols is also by now well known. The two most common polymer-modified polyols are the so-called PIPA (PolyIsocyanate PolyAddition) polyols and the PHD (PolyHarnstoff Dispersion) polyols. Both these polymer-modified polyols and others are prepared by the addition polymerization of an isocyanate, for example a di- or polyisocyanate, with an isocyanate-reactive monomer, preferably an amino-functional compound: an alkanolamine in the case of PIPA polyols, and a di- or polyamine in the case of PHD polyols. Mixtures of these isocyanate reactive monomers as well as reactive diols may also be used. The reactive monomers are polymerized in situ in a polyoxyalkylene polyether polyol which forms the continuous phase of the polymer-modified polyol. In many cases, a portion of the polyol continuous phase becomes associated with the polymer phase by reaction with isocyanate groups. More detailed description of polymer-modified polyols is presented hereinafter.

In both polymer polyols and polymer-modified polyols, the monomers are generally initially soluble in the polyol continuous phase, as are in general the initial low molecular weight oligomers. However, as the molecular weight of the polymer phase grows, the polymer becomes insoluble, forming small particles which rapidly coalesce and/or agglomerate to larger particles in the submicron to several micron range. Hereinafter, the term "polymer polyol" will refer to dispersions of vinyl polymers, "polymer-modified polyol" to polyurea, polyurethaneurea, or other isocyanate-derived polymer dispersions, and the term "polyol polymer dispersions" will refer to both of these collectively.

The base polyols used in preparing polyol polymer dispersions generally contain a high proportion of polyoxypropylene moieties. Polyoxypropylene polyether polyols are conventionally prepared by the base-catalyzed oxyalkylation of a suitably functional initiator molecule with propylene oxide or a mixture of propylene oxide and ethylene oxide. During base-catalyzed oxypropylation, a competing rearrangement of propylene oxide into allyl alcohol continually introduces this unsaturated monol into the polymerization reactor. The allyl alcohol acts as an additional initiator, and being monofunctional, lowers the actual functionality of the polyol. The continued creation of low molecular weight monofunctional species also broadens the molecular weight distribution. As a result of these effects, the practical upper limit of polyoxypropylene polyether polyols equivalent weight is c.a. 2000 Da (Daltons).

For example, a 4000 Da molecular weight base-catalyzed polyoxypropylene diol may contain 0.07 to 0.12 meq. unsaturation per gram polyol, amounting to from 25–40 mol percent of monol. As a result, the polyol nominal functionality of two is reduced to actual functionalities of c.a. 1.6 to 1.7 or less. Unsaturation is generally measured in accordance with ASTM test D-2849-69 "Testing Urethane Foam Polyol Raw Materials."

Lowering the oxypropylation temperature and decreasing the amount of basic catalyst allows for some reduction of unsaturation, but at the expense of greatly extended reaction time which is not commercially acceptable. Moreover, the reduction in unsaturation is but slight. Use of alternative catalyst systems, for example cesium hydroxide rather than the more commonly used sodium or potassium hydroxides; strontium or barium hydroxides; dialkyl zinc; metal naphthenates; and combinations of metal naphthanates and tertiary amines have all been proposed. However, the unsaturation is generally reduced only to about 0.03 to 0.04 meq/g by these methods, still representing 10–15 mol percent monol. In all these cases, the catalyst residues must be removed prior to the in situ polymerization of vinyl or other monomers to produce polyol polymer dispersions. Basic catalysts are generally removed by adsorption with magnesium silicate followed by filtration, by neutralization followed by filtration, or through the use of ion-exchange techniques.

In the 1960's, double metal cyanide catalysts such as complexes of zinc hexacyanocobaltate were found to be useful in a variety of polymerization reactions, as evidenced by U.S. Pat. Nos. 3,427,256, 3,427,334, 3,427,335, 3,829,505, 3,941,849, and 4,242,490. In polymerization of propylene oxide, such catalysts were found to produce polyols with unsaturation in the range of 0.02 meq./g. However, even though relatively active catalysts, their cost relative to activity was quite high. In addition, catalyst removal was problematic. Refinements in double metal cyanide complex catalysts have led to catalysts with somewhat higher activity, as evidenced by U.S. Pat. Nos. 4,472,560, 4,477,589, 4,985,491, 5,100,997, and 5,158,922. These catalysts, generally glyme complexes of zinc hexacyanocobaltate, were effective in preparing polyoxypropylene polyols with unsaturation levels of c.a. 0.015 to 0.018 meq/g. Despite being more active than the prior catalysts, the cost of these improved catalysts, in addition to the difficulties associated with catalyst removal, again prevented any large scale commercialization.

Recently, however, exceptionally active double metal cyanide complex catalysts have been developed at the ARCO Chemical Co., as evidenced by copending U.S. application Ser. No. 08/156,534 now U.S. Pat. No. 5,470,813 and application Ser. No. 08/302,296 now U.S. Pat. No. 5,482,908, herein incorporated by reference. In addition to their much higher activity as compared to previous double metal cyanide complex catalysts, these catalysts have further been shown suitable for producing polyoxypropylene polyols with measured unsaturation in the range of 0.003 to 0.007 meq/g. Not only is the measured unsaturation exceptionally low, but moreover, despite the fact that unsaturation is generally accepted as a measure of monol content, lower molecular weight species are not detected by gel permeation chromatography. The polyoxypropylene polyols are truly monodisperse, having a very narrow molecular weight distribution. Despite being much more active catalysts than prior catalysts and being more susceptible to simple filtration for catalyst removal, the necessity to finely filter or otherwise remove catalyst residues prior to use as base polyols for polyol polymer dispersion production undesirably increases processing time.

In Japanese published application H2-294319 (1990), double metal cyanide complex catalysts were used to prepare polyoxypropylene polyols following which the double metal cyanide catalyst residues were denatured by adding alkali metal hydroxide which then served as the oxyalkylation catalyst for capping the polyoxypropylene polyols with oxyethylene moieties. Following removal of the catalyst residues, high primary hydroxyl content polymer polyols were prepared in a conventional manner. Similar polymer polyols prepared by in situ polymerization in oxyethylene capped polyoxypropylene polyols are disclosed in U.S. Pat. Nos. 5,093,380 and 5,300,535.

In Japanese published application 5-39428 (1993), unspecific zinc hexacyanocobaltate catalysts were used to prepare polyoxypropylene polyols which were then used as base polyols for polymer polyol manufacture, with or without further addition of double metal cyanide catalyst as a vinyl polymerization catalyst. However, the presence of large amounts of double metal cyanide catalyst residues in the polymer polyol product, even if they did not affect subsequent in situ vinyl polymerization, is undesirable. In the food processing industry and medical prostheses industries, for example, heavy metal ion content must be minimal.

J. L. Schuchardt and S. D. Harper, "Preparation Of High Molecular Weight Polyols Using Double Metal Cyanide Catalysts, " 32ND ANNUAL POLYURETHANE TECNIAL MARKETING CONFERENCE, Oct. 1–4, 1989, discloses that double metal cyanide complex catalyst residues can increase the viscosity of isocyanate-terminated prepolymers prepared from polyols containing such residues, this viscosity increase believed due to allophanate formation. Herrold et al. in U.S. Pat. No. 4,355,188 and the many other patents directed to removal of catalyst residues, e.g., U.S. Pat. Nos. 3,427,256, 5,248,833, 4,721,818, 5,010,047, and 4,987,271 attest to the commercial significance of double metal cyanide catalyst removal.

It would be desirable to provide a method of preparing polyol polymer dispersions from double metal cyanide catalyzed pqlyoxypropylene polyether polyols without the necessity of removing or denaturing double metal cyanide complex catalyst residues, without such catalyst residues appearing in the continuous polyol phase of the polyol polymer dispersion. It would be further desirable to prepare polymer polyols which are white or off-white in color.

SUMMARY OF THE INVENTION

It has now been surprisingly discovered that polyol polymer dispersions may be prepared from certain double metal cyanide complex-catalyzed polyoxypropylene polyether polyols without removing the double metal is cyanide complex catalyst residues, while obtaining polyol polymer dispersions containing only exceptionally low levels of catalyst residues in the continuous polyol portion of the polyol polymer dispersion. The polymer polyols of the subject invention are generally white to off-white in color, and may be stored without concern of gradual precipitation of double metal cyanide complex residue solids or generation of carbonyl group-containing polyether polyol decomposition products. Catalyst levels in polyurethane foam formulations employing polyol polymer dispersions of the subject invention can unexpectedly be reduced from levels required for preparing foam from dispersions employing conventional polyols as the base polyol.

DESCRIPTION OF THE PREFERRED EMBODIMENTS

The polyoxyalkylene polyols used as base polyols for the subsequent manufacture of polyol polymer dispersions include at least one polyoxyalkylene polyether polyol prepared by the polymerization of propylene oxide onto one or more initiator molecules of suitable functionality, optionally in conjunction with one or more alkylene oxides other than propylene oxide, in the presence of an encapsulative double metal cyanide complex catalyst as hereinafter defined. The alkylene oxides other than propylene oxide which may optionally be used in conjunction with the latter include, but are not limited to, ethylene oxide, 1,2- and 2,3-butylene oxide, styrene oxide, $C_{5-20}$ α-olefin oxides, epichlorohydrin, drin, chlorinated butylene oxides, and the like. Ethylene oxide is particularly preferred. When an additional alkylene oxide other than ethylene oxide is used together with propylene oxide, the additional alkylene oxide may be added to the polymerization at any stage, either alone, or with additional propylene oxide, to form block, random, or block/random polyoxyalkylene polyether polyols. However, when ethylene oxide is used as the additional alkylene oxide, the ethylene oxide must be added together with propylene oxide or other higher alkylene oxide to form random or block/random polyoxyalkylene polyols. Polyoxyalkylation with ethylene oxide alone has been found to result in products believed to contain large quantities of polyoxyethylene instead of the desired oxyethylene blocks or caps in the polyoxyalkylene polyol.

Suitable initiator molecules include the di- to octafunctional, conventional initiator molecules, for example, ethylene glycol, propylene glycol, glycerine, trimethylolpropane, pentaerythritol, sorbitol, sucrose. and the like. However, it has been found that double metal cyanide complex-catalyzed oxyalkylation of low molecular weight initiators, particularly low molecular weight vicinal glycol initiators such as the foregoing, results in low initial oxyalkylation rates as well as an extended "induction period" before significant catalytic activity occurs. Thus, it is preferable to use oligomeric polyoxyalkylation products of the above or other monomeric initiators as initiators for preparing the base polyoxyalkylene polyol.

Suitable oligomeric initiators may be prepared by conventional, base catalyzed oxyalkylation of monomeric initiators, or by catalysis with alternative catalysts such as diethylzinc, calcium naphthenate, and the like. The particular catalyst is not critical, however, when basic catalysts are used, the catalyst residues should be removed from the oligomeric initiator by conventional treatment prior to continued oxyalkylation employing double metal cyanide complex catalysts; otherwise, the latter may be inactivated. The oligomeric initiators may comprise monomeric initiators oxyalkylated with propylene oxide, mixtures of propylene oxide and ethylene oxide or another alkylene oxide, higher alkylene oxides, or all ethylene oxide. Preferable are oligomeric initiators prepared from all propylene oxide or mixtures of propylene oxide and ethylene oxide. The oligomeric initiators preferably have equivalent weights of from 100 Da to 1000 Da, preferably from 150 Da to 500 Da. Molecular weights and equivalent weights herein in Da (Daltons) are number average molecular weights and number average equivalent weights, respectively, unless otherwise designated.

The oxyalkylation conditions for preparation of the base polyol are those conventionally used in double metal cyanide complex oxyalkylation. The initiator, preferably an oligomeric polyoxyalkylene polyol initiator, is charged to an agitated reactor, the double metal cyanide complex catalyst added, and the reactor purged with nitrogen. Propylene oxide is added at the desired oxyalkylation temperature, generally from 50° C. to 160° C., more preferably from 70° C. to 130° C., and the reactor pressure monitored until a pressure drop is observed, indicating the end of the induction period. Additional propylene oxide, optionally in conjunction with other alkylene oxide, is then added until the desired molecular weight is achieved. Reaction pressure is generally kept below 6 bar. Following alkylene oxide addition, the reactor is maintained at the oxyalkylation temperature for a period to allow unreacted alkylene oxide to react, the reactor vented, and any remaining alkylene oxide stripped off at modest to low vacuum, optionally with the use of a nitrogen stream.

In the past, following preparation of polyoxyalkylene polyols by the above method, the polyol product has been treated to remove residual double metal cyanide catalyst, by filtration, denaturing, treatment with chelating agents, or combinations of these methods. However, in the practice of the subject invention, it is not necessary to remove the double metal cyanide complex catalyst residues to the extent necessary for conventional polyether polyols, provided an encapsulative double metal cyanide complex catalyst is used. It would not depart from the spirit of the invention to rapidly filter the polyoxyalkylene polyol, for example, through a coarse filter to remove a portion of the catalyst residues, or to store the polyol in a non-agitated tank and allow a portion of the catalyst residues to settle out. However, in either case, the amount of residual double metal cyanide complex residues present in the base polyol prior to in situ vinyl polymerization, will normally exceed the limits detectable by Inductively Coupled Plasma sample analysis or other equivalent means of analysis, this limit generally being c.a. 1 ppm. Preferably, the major portion of double metal cyanide complex catalyst residue is not removed from the base polyol.

For example, a polyoxypropylene polyol prepared with an encapsulative zinc hexacyanocobaltate complex catalyst at a catalyst concentration of 250 ppm in the finished polyol, after simple filtration or normal setting upon storage, may contain 47 ppm Zn and 16 ppm Co. Following polymer polyol preparation, the levels of Zn and Co in the polyol polymer dispersion continuous phase may be reduced to 2 ppm Zn and <1 ppm Co, levels which are commercially acceptable. Preparation of base polyols with encapsulative double metal cyanide catalysts at lower catalyst levels and/or by more thorough filtration, with or without additional methods of catalyst removal, may result in Zn and Co levels of, for example 3 ppm and 2 ppm, respectively prior to polymerization to prepare the dispersed phase. While these transition metal levels are low, they may be lowered further by in situ polymerization to form dispersed polymer phase in which the catalyst residues are concentrated in the dispersed phase.

Thus, whether the initial transition metal content is high or low, it is lowered further by the process of the subject invention, provided that an encapsulative double metal cyanide complex catalyst is utilized. It is most surprising that under the same conditions, non-encapsulative double metal cyanide catalysts remain substantially in the continuous phase. The subject process allows encapsulative double metal cyanide complex catalyst residues to be simply left in the polyol without any post-treatment catalyst removal, or post-treatment which removes only a portion of catalyst residues, for example a coarse, rapid filtration which by itself would not be suitable for purification of non-polymer, double metal cyanide complex catalyzed polyols.

The base polyols suitable for use in the process of the subject invention may contain from 4 ppm transition metal content to well over several hundred ppm transition metal content. Preferably, the base polyols contain from 4 ppm to 100 ppm, more preferably from 5 to 50 ppm, and most preferably, from 10–40 ppm transition metal content. The catalyst remaining in the continuous phase following in situ dispersed phase polymerization preferably contains less than 4 ppm total transition metals, more preferably less than 3 ppm, and most preferably less of each metal than a lower limit of detection of c.a. 1 ppm. The advantageous results of the subject process may also be characterized by the degree of catalyst removal from the base polyol into the dispersed polymer phase, regardless of the continuous phase transition metal content. Preferably, 60% or more of the transition metal content of the base polyol is partitioned into the dispersed polymer phase, more preferably 75% or more, and most preferably about 90% or more on a weight basis. Both a high of percentage partitioning and minimal continuous phase transition metal content are of course most desirable.

The polyol polymer dispersions prepared by the subject process are unique products, in that double metal cyanide complex catalyst residues are present in the polymer polyol or polymer-modified polyol as a whole, but concentrated in the dispersed polymer phase and largely absent from the continuous polyol phase. Such polyol polymer dispersions have not been previously disclosed.

The double metal cyanide complex catalysts useful in the subject invention are encapsulative double metal cyanide catalysts. When such catalysts are utilized, the catalyst residues become associated with the polymer particle dispersed phase, and are removed from the continuous polyoxyalkylene polyether polyol phase. While not wishing to be bound by any particular theory, it is believed that the polymer particles actually encapsulate the double metal cyanide complex catalyst residues. It is possible that the polymerizable monomers preferentially polymerize on or proximate to the double metal cyanide complex residues, surrounding the residue with polymer, or that double metal cyanide complex particle residues serve as nucleation sites for polymer particle agglomeration or coagulation, or that the polymer particles or agglomerates serve as adsorbent sites for the catalyst residues.

By whatever mechanism or combination of mechanisms which is/are operable, the net result is that double metal cyanide complex residues are removed from the continuous polyoxyalkylene polyether polyol phase. When the discontinuous polymer phase is separated from the polyol phase by means of filtration or centrifugation, it is found that when an encapsulative double metal cyanide complex catalyst is used, the polymer particles contain virtually all catalyst residues and the polyol phase contains little or none. The measured amounts of transition metals, for example, zinc and cobalt, in the continuous polyoxyalkylene polyol component are close to or below the common limits of detection. Thus, the term "encapsulative double metal cyanide catalyst" refers to a double metal cyanide catalyst which becomes associated with the polymer particles of the dispersed polymer phase in polyol polymer dispersions such that no substantial amount of double metal cyanide catalyst remains in the continuous polyol phase. At least 75 weight percent of double metal cyanide complex residues, as measured by total Zn/Co concentrations, should preferably be removed from the continuous polyol phase.

It has been surprisingly found that the double metal cyanide complex catalysts utilized in the prior art, zinc hexacyanocobaltate-glyme catalysts, are not encapsulative double metal cyanide catalysts. Residues of such catalysts, as shown by Comparative Example 5 herein, remain in most substantial part in the continuous polyol phase. To determine whether any particular double metal cyanide complex catalyst is an encapsulative double metal cyanide complex catalyst, a simple test may be performed. In this test, the double metal cyanide complex catalyst under consideration is used to prepare a polyoxyalkylene polyether base polyol by oxyalkylating a 200–500 Da equivalent weight oligomeric polyoxypropylene initiator in the presence of from 25 ppm to 250 ppm double metal cyanide complex catalyst based on the weight of the base polyol product. The amounts of transition metals in the polyol product, for example Co and Zn, are measured, for example by Inductively Coupled Plasma techniques, and a polymer polyol prepared by the in situ polymerization of a 1:2 mixture of acrylonitrile and styrene in the presence of an effective amount of a vinyl polymerization initiator, for example 0.5 weight percent azobisisobutryronitrile, to form a polymer polyol having a dispersed phase which constitutes from 20 to 50 percent by weight of the polymer polyol product. The dispersed polymer phase is then separated from the continuous polyol phase and the transition metal content of the polyol phase determined. If the polyol phase contains less than 25% total transition metal as compared to the amount present in the base polyol prior to in situ vinyl polymerization, or if regardless of the relative percentage the transition metal contents of the continuous polyol phase are lowered from higher levels to approximately the limits of detection or below (1–2 ppm), then the catalyst is an encapsulative double metal cyanide complex catalyst. The encapsulative double metal cyanide complex catalysts identified by this test may be used to prepare both the polymer polyols and polymer-modified polyols of the subject invention.

Suitable encapsulative double metal cyanide complex catalysts are disclosed in copending U.S. application Ser. No. 08/156,534 and copending U.S. Ser. No. 08/302,296, which are herein incorporated by reference. Examples of encapsulative double metal cyanide complex catalysts are given herein in Examples 1–6. While the descriptions herein and test methodology have been illustrated by the use of the preferred zinc hexacyanocobaltate complex catalysts, it is to be understood that encapsulative double metal cyanide complexes of other metals may be used as well. In such cases, the definitions, ranges, limitations, etc., presented herein with respect to Co and Zn should be equated with the same limitations for the particular metals involved, for example Zn and Fe for zinc hexacyanoferrates; Ni and Fe for nickel hexacyanoferrates; and Fe and Cr for iron(II) hexacyanochromate. Due to their generally higher catalytic activity, complexes containing zinc as the cation and cobalt in the cyanide-containing anion are highly preferred. For purposes of definition of catalyst residues in ppm, a theoretical metal atomic weight of 62 is assumed. The corresponding ppm level for any given metal may be found by multiplying a particular metal residue level by the appropriate atomic weight/theoretical metal atomic weight ratio. For example, if the metal were vanadium with an atomic weight of approximately 51 amu, a 5 ppm metal residual level would become 5 ppm×(51/62).

Preferred complexing agents for preparing the encapsulative double metal cyanide complex catalysts are t-butanol and combinations of t-butanol with one or more oligomeric polyoxyalkylene polyether polyols, preferably polyether polyols at least partially terminated with a tertiary hydroxyl moiety. The polyether polyol complexing agents preferably have equivalent weights greater than 200 Da, more preferably greater than 500 Da, and most preferably in the range of 1000 Da to 3000 Da. The encapsulative double metal cyanide complex catalysts are, in general, non-stoichiometric complexes which are substantially amorphous as shown by the virtual absence of sharp lines in their x-ray diffraction spectra corresponding to crystalline double metal cyanide itself, i.e., zinc hexacyanocobaltate in the case of zinc hexacyanobaltate complex catalysts. The catalysts also, in general, have measurably greater particle sizes than prior art catalysts, such as the conventionally prepared zinc hexacyanobaltate-glyme catalysts.

The in situ vinyl polymerization used to prepare polymer polyols is conventional except for the presence of the encapsulative double metal cyanide complex residues. Examples of suitable polymer polyol preparation may be found in U.S. Pat. Nos. 3,304,273, 3,383,351, 3,652,639, 3,655,553, 3,823,201, 3,953,393, 4,119,586, 4,524,157, 4,690,956, 4,997,857, 5,021,506, 5,059,641, 5,196,746, and 5,268,418, which are herein incorporated by reference. Either batch processes, semi-batch, or fully continuous methods of preparation may be used. Continuous processes are preferred.

In the semi-batch process, a reactor vessel equipped with an efficient means of agitation, for example an impeller-type stirrer or recirculation loop, is charged with from 30% to 70% of total base polyol. To the reactor is then added the polymerizable vinyl monomers dissolved in additional polyol. Vinyl polymerization catalyst may be added to the vinyl monomer solutions, which are maintained at relatively low temperature prior to addition to the reactor, or may be added as a separate stream. The reactor itself is maintained at a temperature such that the polymerization catalyst is activated. In most cases, the vinyl polymerization catalyst is a free radical polymerization initiator. Following addition of the desired quantity of vinyl monomers, the reactor is allowed to "cook out" to substantially complete vinyl polymerization, following which residual unreacted monomers may be removed by stripping.

A continuous process may be implemented in one or more reactors in series, with the second reactor facilitating substantially complete reaction of vinyl monomers with continuous product takeoffs, or may be performed in a continuous tubular reactor with incremental additions of vinyl monomers along the length of the reactor.

The preferred vinyl monomers are styrene and acrylonitrile. However, many vinyl monomers are suitable, non-limiting examples being methylacrylate, methylmethacrylate, a-methylstyrene, p-methylstyrene, methacrylonitrile, vinylidene chloride, and the like. Lists of suitable vinyl monomers may be found in the references previously cited. Mixtures of vinyl monomers are advantageously used, preferably mixtures of acrylonitrile and styrene in weight ratios of 10:1 to 1:10, more preferably 1:4 to 4:1, and most preferably 1:1 to 1:3. Mixtures of vinyl monomers comprising about 50 weight percent or more of styrene with one or more monomers other than styrene are particularly preferred.

The polymerization catalyst is preferably a free radical polymerization initiator such as an azobisalkylnitrile, for example azobis(isobutryonitrile) (AIBN), azobis(4-cyanovaleric acid), azobis(dimethyl-valeronitrile), preferably AIBN; peroxy compounds, for example, peroxyesters and peroxyketones, and the like. Redox polymerization initiators may also be used.

The in situ vinyl polymerization is preferably conducted in the presence of a stabilizer or stabilizer precursor. Stabilizer precursors may comprise one or more polyoxyalkylene moieties bonded to a group which can participate in vinyl polymerization, preferably a reactive, unsaturated ethylenic group. Examples of stabilizers and stabilizer precursors are contained in the previously cited patents, and include polyetherester polyols prepared by reacting maleic anhydride with a polyoxyalkylene polyol and capping the remaining free carboxyl group of the half-ester with an alkyl or polyoxyalkyl group; the reaction product of isocyanatoethylacrylate or like compounds with a polyoxyalkylene polyol; or the reaction product of other unsaturated isocyanates, i.e., TMI, 1-(1-isocyanato-1-methylethyl)-3-methylethenyl)benzene with a polyoxyalkylene polyol. The stabilizer precursor may be present in the reaction mixture to the extent of less than 0.01 to about 0.3 mol percent, preferably 0.01 to about 0.1 mol percent.

Reaction moderators and polymer control agents may also be present. Reaction moderators fall within the general class of chain transfer agents, and are believed to limit the molecular weight of the vinyl polymers produced. Examples of reaction moderators include alkanols such as isopropanol and isobutanol; mercaptans such as dodecylmercaptan; halogenated hydrocarbons, particularly those containing bromine and/or iodine, and the like. Further examples of reaction moderators may be found in the patents previously cited. Polymer control agents include low molecular weight liquids not conventionally viewed as chain transfer agents, as described in U.S. Pat. No. 4,652,589, herein incorporated by reference. Suitable polymer control agents include water, cyclohexane, and benzene.

As previously discussed, polymer-modified polyols are prepared by in situ polymerization of one or more di- or polyisocyanates with isocyanate-reactive components, which may be a portion of the isocyanate itself. For example, polymerization of a di- or poly-isocyanate with itself in the presence of a suitable catalyst may be used to form polyisocyanate dispersions (PID), or dispersions containing a variety of isocyanate-derived linkages such as isocyanurate, allophanate, uretonimine, uretdione, carbodiimide and the like, often in association with reaction of a portion of the polyol continuous phase to introduce urethane linkages, or when an amino-functional species is present, urea linkages.

However, the preferred polymer-modified polyols are those prepared by the in situ polymerization of a di- or polyisocyanate with an amino-functional monomer, preferably a diamino-functional monomer, or an alkanolamine monomer, to form PHD and PIPA polymer-modified polyols. Preparation of polymer-modified polyols by reaction of alkanolamine/isocyanate reaction mixtures in Biitu is described in U.S. Pat. Nos. 4,293,470; 4,296,213; 4,374,209; 4,452,923; and PCT published application WO 94/12553, all herein incorporated by reference. In general, a mono- to trialkanol-amine having from two to about 8 carbons in the alkanol residue such as ethanolamine, diethanolamine, triethanolamine, diisopropanolamine, triisopropanolamine, N-methylisopropanolamine, 2-(2-aminoethoxy)ethanol, hydroxyethylpiperazine, or the like is dissolved in a polyoxyalkylene base polyol, and di- or polyisocyanate, preferably TDI or MDI is added dropwise with stirring, during the course of which the temperature generally rises to about 40–50° C. Catalysts are generally unnecessary, although in some cases catalysts such as stannous octoate or dibutyltin dilaurate may be added. The reaction is generally allowed to proceed for a period of from 0.5 to 2 hours, during the course of which a white dispersion is obtained. In general, a portion of the polyol will also react, as described in Goethals, Ed., TELECHELIC POLYMERS: SYNTHESIS AND APPLICATIONS, CRC Press, Inc., Boca Raton, Fla., © 1989, p. 211.

In PCT published application WO 94/12553 is disclosed an improved, substantially continuous process for preparing PIPA polyols with high solids content and minimal viscosity. In the process disclosed, a polyoxy-alkylene base polyol is mixed with a first alkanolamine such as triethanolamine, and fed to a high pressure mixhead calibrated to provide the desired amount of isocyanate, preferably polymeric diphenylmethane diisocyanate or an 80:20 mixture of 2,4- and 2,6-toluene-diisocyanates. A short time later, e.g. 5 seconds, a further quantity of alkanolamine, which may be the same or different from the first, is added to the reactive mixture in a second high pressure mixhead. By this process, stable, non-gelling, high solids dispersions of useable viscosity are obtained with solids contents in some cases in excess of 50% by weight.

PHD polymer-modified polyols are also preferred polymer-modified polyols. Such polyols are described in Goethals, op. cit., U.S. Pat. Nos. 3,325,421; 4,042,537; and 4,089,835; and also in M. A. Koshute et al., "Second Generation PHD Polyol For Automotive Flexible Molding", POLYURETHANES WORLD CONGRESS, Sep. 29, 1987—Oct. 2, 1987, pp. 502–507; and K. G. Spider et al., "PHI Polyols, A New Class of PUR Raw Materials," J. CELL PLAS., January/February 1981, pp. 43–49, all herein incorporated by reference.

In general, as with PIPA polyols, the isocyanate-reactive monomer, in this case an amine or polyamine, is added to the base polyol. For amines with low solubility, high speed stirring is used to form a fine dispersion. Isocyanate is then added slowly, during the course of which the temperature will rise. Following a period of time to allow for full reaction, a white, polyurea dispersion is obtained. The polymer particles incorporate a portion of the polyol continuous phase. Preferred diamines are hydrazine and ethylenediamine, although other diamines as well as hydrazides, are useful. Preferred isocyanates are commercial aromatic isocyanates such as methylene diphenylene diisocyanate, toluene diisocyanate, polyphenylene polymethylene polyisocyanate, and the like, including modified isocyanates such as urethane-, urea-, carbodiimide-, uretdione-, uretonimine-, and allophanate-modified isocyanates. Aliphatic isocyanates such as hexamethylene diisocyanate and isophorone diisocyanate are also useful in manufacturing PHD (and PIPA) polymer-modified polyols. Solids levels of 10–40% or more are useful, in particular 10 or 20 to about 30%. Continuous processes, as disclosed in U.S. Pat. No. 4,089,835 are useful.

The base polyol used for in situ polymerization to form polyol polymer dispersions should comprise in major part a polyoxyalkylene polyol containing a substantial quantity of oxypropylene moieties prepared in the presence of an encapsulative double metal cyanide catalyst, preferably at least S ppm of which, calculated as Co and Zn or the corresponding equivalents of other metals on a weight/weight basis, remain in the polyol. Preferably, this major component of the base polyol is not subjected to catalyst removal treatment other than an optional coarse filtration to remove gross particulates or by natural sedimentation of catalyst residues in a non-agitated holding tank. This major portion of polyoxyalkylene (>50 weight percent) may be mixed with other base polyol components such as conventionally catalyzed polyoxyalkylene polyether polyols, polyester polyols, polyetherester polyols, and the like. However, if polyoxyalkylene polyols prepared from non-encapsulative double metal cyanide catalysts are used, either the non-encapsulative double metal cyanide catalyst residues must be substantially completely removed, or the amount of such polyol restricted such that no more than 3–4 ppm non-encapsulative double metal cyanide complex catalyst residue calculated on the basis of Co and Zn or their other-metal equivalents is present in the base polyol.

The functionality of the polyoxyalkylene polyether polyol component may range from less than two, to eight or more, preferably from two to eight and more preferably from two to six. The functionality for any given base polyol component is dependent on the desired end use. For example, elastomers generally require low functionalities, e.g., two to three, while polyurethane foams generally require functionalities from 2.5 to 4.0. "Functionality" as used herein is meant the mol average nominal functionality. "Nominal" functionality is the theoretical functionality based on the number of oxyalkylatable groups on the initiator molecule.

The hydroxyl number of the base polyol may range from about five to in excess of 100, but is preferably within the range of 10–70, and more preferably in the range of 20–60. Hydroxyl number may be measured in accordance with ASTM D-2849-69. The hydroxyl number and functionality of the polyol polymer dispersion may be adjusted post manufacture by the addition of polyols other than the base polyol used for the in situ polymerization. Solids contents of the polyol polymer dispersions range from about 10 weight percent to about 60 weight percent or more based on total polymer polyol weight. Polymer polyols are preferably prepared with solids contents in the higher ranges, i.e., 25 to 60 weight percent, more preferably 30 to 50 weight percent, and reduced in solids content where appropriate by blending with additional polyol. In this manner, reactor capacity and product throughput are maximized. Polymer-modified polyols generally contain somewhat lower levels of solids to limit viscosity of the polymer-modified polyol product. Solids contents of from 10 to 50 weight percent, more preferably from 10 to 30 weight percent are suitable.

Double metal cyanide complex catalyst sample x-ray diffraction spectra were analyzed using monochromatized CuKa, radiation ($\lambda$=1.54059 Å) . A Seimens D500 Kristalloflex diffractometer powered at 40 kV and 30 mA was operated in a step scan mode of 0.02° 2 $\theta$ with a counting time of 2 seconds/step. Divergence slits of 1° in conjunction with monochrometer and detector apertures of 0.05° and 0.15° respectively. Each sample was run from 5° to 70° 2 $\theta$. Water of hydration can cause minor variations in measured d-spacings.

The following procedures may be used to determine catalyst activity. A one-liter stirred reactor is charged with polyoxypropylene triol (700 mol. wt.) starter (70 g) and zinc hexacyanocobaltate catalyst (0.057 to 0.143 g, 100–250 ppm level in finished polyol). The mixture is stirred and heated to 105° C. and is stripped under vacuum to remove traces of water from the triol starter. The reactor is pressurized to about 1 psi with nitrogen. Propylene oxide (10–11 g) is added to the reactor in one portion, and the reactor pressure monitored carefully. Additional propylene oxide is not added until an accelerated pressure drop occurs in the reactor; the pressure drop is evidence that the catalyst has become activated. When catalyst activation is verified, the remaining propylene oxide (490 g) is added gradually over about 1–3 h at a constant pressure of 20–24 psi. After propylene oxide addition is complete, the mixture is held at 105° C. until a constant pressure is observed. Residual unreacted monomer is then stripped under vacuum from the polyol product, and the polyol is cooled and recovered.

The reaction rate is determined from a plot of PO consumption in grams versus reaction time in minutes. The slope of the curve at its steepest point is measured to find the reaction rate in grams of PO converted per minute. The intersection of this line and a horizontal line extended from the baseline of the curve is taken as the induction time (in minutes) required for the catalyst to become active.

Polyurethane foams, particularly water-blown flexible polyurethane foams, are prepared by reacting a polyol component with an isocyanate component. The polyol component often contains a polymer polyol or polymer-modified polyol, with or without additional non-ppolymer polyol. In general, tin catalysts and amine catalysts are necessary to produce a stable foam. It has been surprisingly discovered that when the polyol polymer dispersions of the subject invention such as the PIPA polymer-modified polyols are used in the polyurethane foam polyol component, the amount of catalyst, particularly tin catalyst, may be lowered significantly while still producing a stable foam, as compared with otherwise similar formulations where polymer-modified is polyols prepared from conventionally catalyzed (basic catalysis) base polyols are used to prepare the polymer-modified polyol. This unexpected result allows greater processing latitude as well as being more cost effective.

Having generally described this invention, a further understanding can be obtained by reference to certain specific examples which are provided herein for purposes of illustration only and are not intended to be limiting unless otherwise specified.

EXAMPLES 1–6 AND COMPARATIVE EXAMPLE 1

Double Metal Cyanide Catalyst Preparation

Example 1

Potassium hexacyanocobaltate (8.0 g) is added to deionized water (150 mL) in a beaker, and the mixture is blended with a homogenizer until the solids dissolve. In a second beaker, zinc chloride (20 g) is dissolved in deionized water (30 mL). The aqueous zinc chloride solution is combined with the solution of the cobalt salt using a homogenizer to intimately mix the solutions. Immediately after combining the solutions, a mixture of tert-butyl alcohol (100 mL) and deionized water (100 mL) is added slowly to the suspension of zinc hexacyanocobaltate, and the mixture is homogenized for 10 min. The solids are isolated by centrifugation, and are then homogenized for 10 min. with 250 mL of a 70/30 (v:v) mixture of tert-butyl alcohol and deionized water. The solids are again isolated by centrifugation, and are finally homogenized for 10 min. with 250 mL of tertbutyl alcohol. The catalyst is isolated by centrifugation, and is dried in a vacuum oven at 50° C. and 30 in. (Hg) to constant weight. The catalyst exhibits a propylene oxide initial polymerization rate of 10.5 g propylene oxide/min. at 105° C. with a catalyst concentration of 250 ppm based on weight of product polyol, showed no sharp lines in the X-ray diffraction (XRD) spectrum at d-spacings of 5.07, 3.59, 2.54 and 2.28, and had a surface area of 14 m$^2$/g.

Example 2

The procedure of Example 1 is modified as follows. Isopropyl alcohol is substituted for tert-butyl alcohol. Following combination of the zinc S chloride and potassium hexacyanocobaltate solutions and homogenization in the presence of isopropyl alcohol, the catalyst slurry is filtered through a 0.45 micron filter at 20 psi. The washing steps of Example 1 are also repeated, but filtration rather than centrifugation is used to isolate the catalyst. The washed catalyst is dried to constant weight as described above. The catalyst exhibits a propylene oxide initial polymerization rate of 1.70 g/min., and exhibited the same lack of sharp peaks in the XRD spectrum as the catalyst of Example 1.

Example 3

Potassium hexacyanocobaltate (8.0 g) is dissolved in deionized (DI) water (140 mL) in a beaker (Solution 1). Zinc chloride (25 g) is dissolved in DI water (40 mL) in a second beaker (Solution 2). A third beaker contains Solution 3: a mixture of DI water (200 mL), tert-butyl alcohol (2 mL), and polyol (2 g of a 4000 mol. wt. polyoxypropylene diol prepared via double metal cyanide catalysis.

Solutions 1 and 2 are mixed together using a homogenizer. Immediately, a 50/50 (by volume) mixture of tert-butyl alcohol and DI water (200 mL total) is added to the zinc hexacyanocobaltate mixture, and the product is homogenized for 10 min. Solution 3 (the polyol/water/tert-butyl alcohol mixture) is added to the aqueous slurry of zinc hexacyanocobaltate, and the product is stirred -magnetically for 3 min. The mixture is filtered under pressure through a 5-$\mu$m filter to isolate the solids.

The solid cake is reslurried in tert-butyl alcohol (140 mL), DI water (60 mL), and additional 4000 mol. wt. polyoxypropylene diol (2.0 g), and the mixture is homogenized for 10 min. and filtered as described above, following which the solid cake is again reslurried in tert-butyl alcohol (200 mL) and additional 4000 mol. wt. polyoxypropylene diol (1.0 g), homogenized for 10 min., and filtered. The resulting solid catalyst is dried under vacuum at 50° C. (30 in. Hg) to constant weight. The yield of dry, powdery catalyst is 10.7 g.

Elemental, thermogravimetric, and mass spectral analyses of the solid catalyst show: polyol=21.5 wt. %; tert-butyl alcohol=7.0 wt. %; cobalt=11.5 wt. %. The catalyst exhibited a propylene oxide polymerization rate of 3.3 Kg propylene oxide/g Co/min. and exhibited the same lack of sharp lines in the XRD spectrum as the catalysts of Examples 1 and 2.

Example 4

A one-gallon glass pressure reactor is charged with a solution of potassium hexacyanocobaltate (40 g) in DI water (700 mL) (Solution 1). Zinc chloride (125 g) is dissolved in a beaker with DI water (200 mL) (Solution 2). Tert-butyl alcohol (500 mL) is dissolved in a beaker with DI water (500 mL) (Solution 3). A fourth mixture (Solution 4) is prepared by suspending a 4000 mol. wt. polyoxypropylene diol (60 g, same as is used in Example 3) in DI water (1000 mL) and tert-butyl alcohol (10 mL).

Solutions 1 and 2 are combined with stirring at 3000 rpm followed immediately by slow addition of Solution 3 to the resulting zinc hexacyanocobaltate mixture. The stirring rate is increased to 900 rpm, and the mixture is stirred for 2 h at room temperature. The stirring rate is reduced to 300 rpm, and Solution 4 is added. The product is mixed for 5 min., and is filtered under pressure as described in Example 1 to isolate the solid catalyst. The solids are reslurried in tert-butyl alcohol (700 mL) and DI water (300 mL), and stirred at 900 rpm for 2 h. The stirring rate is reduced to 300 rpm, and 60 g of the 4000 mol. wt. polyoxypropylene diol is added. The mixture is stirred for 5 min., and is filtered as described above.

The solids are reslurried in tert-butyl alcohol (1000 mL) and stirred at 900 rpm for 2 h. The stirring rate is reduced to 300 rpm, and 30 g of the 20. 4000 mol. wt. polyoxypropylene diol is added. The mixture is stirred for 5 min., and is filtered as described above. The resulting solid catalyst is dried under vacuum at 50° C. (30 in. Hg) to constant weight. The catalyst is easily crushed to a fine, dry powder.

Elemental, thermogravimetric, and mass spectral analyses of the solid catalyst show: polyol=45.8 wt. %; tert-butyl alcohol=7.4 wt. %; cobalt=6.9 wt. %. The catalyst exhibits a propylene oxide polymerization rate of 6.69 g propylene oxide/g Co/min., and exhibited the same lack of sharp peaks in the XRD spectrum as the catalysts of Examples 1–3.

Example 5

The procedure of Example 1 is followed, except that the 4000 mol. wt. polyoxypropylene diol is replaced with a 2000 mol. wt. polyoxypropylene diol also made using double metal cyanide catalysis.

Elemental, thermogravimetric, and mass spectral analyses of the solid catalyst show: polyol=26.5 wt. %; tert-butyl alcohol=3.2 wt. %; cobalt=11.0 wt. %. The catalyst exhibited a propylene oxide polymerization rate of 2.34 Kg propylene oxide/g Co/min., and exhibited the same lack of sharp peaks in the XRD spectrum as the catalysts of Examples 1–4.

Example 6

Example 4 is repeated, except that a 4000 Da diol end-capped with isobutylene oxide to provide c.a. 50% tertiary hydroxyl groups is used. The catalyst exhibited higher activity than the catalyst of Example 4.

Comparative Example 1

This example demonstrates the preparation of a non-encapsulative double metal cyanide complex catalyst. A solution of zinc chloride (26.65 g; 0.1956 mol) in water (26.65 g) is added rapidly to a well-agitated solution of potassium hexacyanocobaltate (13.00 g 0.0391 mol) in water (263.35 g). The potassium hexacyanocobaltate solution is maintained at 40° C. during addition of the zinc chloride solution. A white precipitate of zinc hexacyanocobaltate particles forms immediately upon addition. After stirring for 15 minutes at 40° C., dimethoxyethane (glyme) (84.00 g; 0.9321 mol) is added to the aqueous catalyst slurry. The resulting mixture is stirred for an additional 30 minutes and the zinc hexacyanocobaltate-dimethoxyethane water complex catalyst recovered by filtration using a horizontal basket centrifugal filter and a light weight nylon fabric filter medium. The filtration rate was relatively fast with minimal clogging of the pores of the filter medium. After washing with 300 mL dimethoxyethane and drying in air at ambient temperature and pressure, the filter cake obtained is quite soft and can be easily crushed to a fine powder.

The catalyst exhibits a propylene oxide polymerization rate of 3.50 g propylene oxide/min.

EXAMPLES 7–15 AND COMPARATIVE EXAMPLES 2–4

Polyoxyalkylene Polyether Polyol Synthesis

A two-gallon stirred reactor is charged with polyoxypropylene triol (700 mol. wt.) starter (685 g) and zinc hexacyanocobaltate catalyst (1.63 g). The mixture is stirred and heated to 105° C., and is stripped under vacuum to remove traces of water from the triol starter. Propylene oxide (102 g) is fed to the reactor, initially under a vacuum of 30 in. (Hg), and the reactor pressure is monitored carefully. Additional propylene oxide is not added until an accelerated pressure drop occurs in the reactor; the pressure drop is evidence that the catalyst has become activated. When catalyst activation is verified, the remaining propylene oxide (5713 g) is added gradually over about 2 h while maintaining a reactor pressure less than 40 psi. After propylene oxide addition is complete, the mixture is held at 105° C. until a constant pressure is observed. Residual unreacted monomer is then stripped under vacuum from the polyol product. When catalyst removal is desired, the hot polyol product is filtered at 100° C. through a filter cartridge (0.45 to 1.2 microns) attached to the bottom of the reactor to remove the catalyst. Residual Zn and Co are quantified by X-ray analysis.

Polyether diols (from polypropylene glycol starter, 450 mol. wt.) and triols are prepared as described above using both encapsulative and non-encapsulative zinc hexacyanocobaltate catalysts. The polyol unsaturation of the polyols produced is presented in Table I.

TABLE I

| Example | Catalyst | Hydroxyl Number and Functionality | Polyol Unsaturation (meq/g) |
|---|---|---|---|
| Comparative Examples 2, 3 & 4 | Comparative Example 1 | 54 (Triol) | 0.016 |
|  |  | 27 (Triol) | 0.017 |
|  |  | 15 (Triol) | 0.019 |
| Example 7 | Example 1 | 27 (Triol) | 0.005 |
| Example 8 |  | 56 (Diol) | 0.004 |
| Example 9 |  | 27 (Diol) | 0.005 |
| Example 10 |  | 14 (Diol) | 0.004 |
| Example 11 | Example 3 | 30 (Triol) | 0.006 |
| Example 12 | Example 4 | 29 (Triol) | 0.004 |
| Example 13 | Example 5 | 31 (Triol) | 0.004 |
| Example 14 | Example 6 | 14 (Diol) | 0.005 |
| Example 15 | Example 6 | 28 (Triol) | 0.004 |

EXAMPLES 16–21 AND COMPARATIVE EXAMPLE 5

Polymer polyols are prepared in a continuous process, in each case employing a preformed stabilizer prepared by capping a maleic anhydride/polyoxypropylene polyol half ester with ethylene oxide and isomerizing the maleate unsaturation to fumarate in the presence of morpholine. The preparation of the preformed stabilizer is in accordance with Example 1 of U.S. Pat. No. 5,268,418, herein incorporated by reference.

A continuous polymerization system was used, 32 employing a tank reactor fitted with baffles and an impeller. The feed components were pumped into the reactor continuously after going through an inline mixer to assure complete mixing of the feed components before entering the reactor. The internal temperature of the reactor was controlled to within ±1° C. at 115° C. The contents of the reactor were well mixed. The product flowed out the top of the reactor and into a second unagitated reactor also controlled within 1° C. The product then flowed out the top of the second reactor continuously through a back pressure regulator adjusted to give about 45 psig pressure on both reactors. The crude product then flowed through a cooler into a collection vessel. Percent by weight polymer in the polymer polyol was determined from analysis of the amount of unreacted monomers present in the crude product. The crude product was vacuum stripped to remove volatiles before testing. All of the polymer polyols were stable compositions. In each Example, the feed rates in parts per hour were as follows: polyol, 236.2; preformed stabilizer 25.2; catalyst (AIBN), 1.5; acrylonitrile, 60.9; styrene, 142.1.

The polyols utilized were prepared in accordance with the foregoing Examples. Polyoxyalkylene content, type (triol, diol), hydroxyl numbers, catalyst type, catalyst concentration during polyol preparation are presented in Table II, as are the polymer solids of the resulting polymer polyols, the initial Zn/Co concentrations in the polyol used to prepare the polymer polyol, the Zn/Co concentrations in the polymer polyol (continuous plus dispersed phases) and the Zn/Co concentrations in the polyol (continuous) phase alone.

prepare the polymer-modified polyol contained 6.7 ppm Zn and 2.8 ppm Co. A white dispersion is obtained having catalyst residues concentrated in the dispersed phase, the

TABLE II

| Example | Base Polyol Catalyst Type (Amount, ppm) | Base Polyol Hydroxyl/ Type | Base Polyol Composition | Zn/Co in Base Polyol As Used (ppm) | Zn/Co in Polymer Polyol (ppm) | Zn/Co in Polyol Continuous Phase (ppm) | Polymer Wt. Solids, % |
|---|---|---|---|---|---|---|---|
| Comparative Example 5 | Comparative Example 1 (125) | 47.2/Triol | 10% EO random | 30/13 | 18/8 | 8/8 | 44.6 |
| 16 | Example 1 (250) | 27.1/Diol | 0% EO | 47/16[2] | 27/10 | 2/<1 | 44.8 |
| 17 | Example 3 (25) | 51.8/Triol | 12% EO random | 2/1[1] | <1/<1 | <1/<1 | 45.1 |
| 18 | Example 1 (25) | 51.7/Triol | 12% EO random | 5/2 | 1.5/<1 | <1/<1 | 45.8 |
| 19 | Example 1 (25) | 51.7/Triol | 12% EO random | 2.8/1.5[1] | 2.1/1.1 | <1/<1 | 45.3 |
| 20 | Example 3 (25) | 52.1/Triol | 12% EO random | 4/2 | 1.7/<1 | <1/<1 | 45.4 |
| 21 | Example 3 (25) | 56.8/Triol | 12% EO random | 3/2 | 2.2/<1 | <1/<1 | 44.9 |

[1]Base polyol was filtered after polyol preparation to remove a substantial portion of catalyst residue prior to use in preparing polymer polyol.
[2]Base polyol was not filtered to remove catalyst residue, but portion of residue had settled out. Supernatent was used for polymer polyol preparation.

As can be seen from Table II, the preparation of polymer polyols from base polyols prepared using prior art double metal cyanide-glyme catalyst, a non-encapsulative double metal cyanide catalyst (Comparative Example 5) showed little reduction in Zn/Co content in the polymer polyol continuous phase despite starting with a relatively low Zn/Co content for this type of catalyzed polyol (Zn/Co=30/13). However, when polymer polyols were prepared using encapsulative double metal cyanide catalysts (Examples 16–21), in each case, substantial reductions of Zn/Co content, generally to levels below the level of detection of c.a. 1 ppm, were obtained, even in the case of high initial transition a metal content as is the case for Example 16. Such polyols are useful in numerous applications where polyols with higher Zn/Co content are unsuitable.

EXAMPLES 22–23

Polymer-Modified Polyol Synthesis

Example 22

To 900 g of a trifunctional polyoxyalkylene polyol having a hydroxyl number of 35, a primary hydroxyl content of 13 percent, and an unsaturation of c.a. 0.0062 meq/g, prepared by the encapsulative double metal cyanide complex catalyzed oxyalkylation of a glycerine-initiated oligomer containing residual double metal cyanide catalyst residues is added 48.7 g trietha-nolamine at a temperature of c.a. 25° C. Following thorough mixing, the agitator is turned up to high speed and 51.7 g toluene diisocyanate is added over a period of approximately 5 seconds under a nitrogen blanket. To the mixture is then added 0.3 g T-12 tin catalyst dissolved in a minor amount of additional polyol. The temperature rises to c.a. 40° C., following which the reaction mixture is stirred under slow speed until cooled. The base polyol used to concentrations of Zn and Co in the continuous polyol phase being only 0.5 ppm and <0.2 ppm, respectively.

Example 23

The process of Example 22 is repeated, but with the reactor charges being 1000 g polyol, 230 g triethanolamine, and 0.03 g T-12 tin catalyst. Following thorough mixing and heating to 54° C., the agitation speed is increased to high and 271.0 g toluene diisocyanate added over a period of 5 seconds. The temperature rapidly rises and reaches a maximum of about 105° C. Approximately 10 seconds after isocyanate addition, 50 g DEOA-LF (diethanolamine low freezing) is added, following which the reaction is allowed to cool with slow agitation. A white, high solids PIPA polymer-modified polyol dispersion is obtained with transition metal content concentrated in the dispersed polymer phase.

Comparative Example 6

A polymer-modified polyol was prepared as in Example 22, using the same proportions of reactants, but employing a conventional base-catalyzed base polyol having a hydroxyl number of 35 and a level of unsaturation of 0.027 meq/g.

EXAMPLES 24–25 AND COMPARATIVE EXAMPLES 7 AND 8

Polyurethane Foam Preparation

A series of all water-blown polyurethane foams were prepared from the subject invention polymer-modified polyols synthesized in accordance with Examples 22 and 23 and a conventional polymer-modified polyol synthesized in accordance with Comparative Example 6. The formulations and foam quality are indicated in Table III below.

TABLE III

| Polymer-Modified Polyol From Example | Example 24 22 | Example 25 23 | Comparative Example 7 C-6 | Comparative Example 8 C-6 |
|---|---|---|---|---|
| Base Polyol | | | | |
| Unsaturation, meq/g | 0.0062 | 0.0062 | 0.027[1] | 0.027[1] |
| OH, % | 35 | 35 | 35 | 35 |
| Primary OH, % | 13 | 13 | 7 | 7 |
| Polymer-Modified Polyol | | | | |
| Base Polyol, g | 900 | 1000 | 900 | 900 |
| Triethanolamine | 48.7 | 230 | 48.7 | 48.7 |
| Tolylene Diisocyanate, g | 51.7 | 271.0 | 51.7 | 51.7 |
| Dibutyl-tin-dilaurate, g | 0.3 | 0.03 | 0.3 | 0.3 |
| Diethanolamine (low freezing), g | — | 50 | — | — |
| Formulation for Foam | | | | |
| PIPA Polyol, g | 100 | 100 | 100 | 100 |
| DEOA-LF, g | 1.18 | 1.18 | 1.18 | 1.18 |
| B-8707 silicone, g | 0.5 | 0.5 | 0.5 | 0.5 |
| Water, g | 2.42 | 2.42 | 2.42 | 2.42 |
| A-1 amine catalyst, g | 0.11 | 0.11 | 0.11 | 0.11 |
| T-12 tin catalyst, g | 0.07 | 0.07 | 0.07 | 0.25 |
| TDI, g | 39 | 39 | 39 | 39 |
| Foam Appearance | Good | Good | Collapses | Very Porous |

[1]Conventional base-catalyzed base polyol.

As can be seen, both the polymer-modified polyols of the subject invention (from Examples 22 and 23) employing low-unsaturation base polyols, foamed well at 0.07 parts tin catalyst per 100 parts polyol, while polymer-modified polyols prepared from conventionally catalyzed base polyols (from Comparative Example 6) did not produce a stable foam at the same catalyst concentration, the foam exhibiting collapse, and produced only a poor quality, very porous foam even at a tin catalyst level higher by a factor of almost four. These results are totally unexpected.

Having now fully described the invention, it will be apparent to one of ordinary skill in the art that many changes and modifications can be made thereto without departing from the spirit or scope of the invention as set forth herein.

What is claimed is:

1. A polymer polyol prepared by the in situ polymerization of one or more vinyl monomers in a base polyol comprising an encapsulative double metal cyanide complex-catalyzed oxypropylene moiety-containing polyoxyalkylene polyether polyol, said polymer polyol having a continuous phase containing said double metal cyanide complex-catalyzed polyether polyol and a dispersed phase comprising vinyl polymer solids, said polymer polyol containing about 4 ppm or more of transition metals derived from said double metal cyanide complex catalyst, at least about 60% of said transition metals associated with said vinyl polymer solids dispersed phase.

2. The polymer polyol of claim 1 wherein said polymer polyol contains in excess of about 5 ppm of transition metals and the total amount of each transition metal in said continuous phase is less than or equal to about 1 ppm.

3. The polymer polyol of claim 1 wherein said polymer polyol contains in excess of about 10 ppm of transition metals and the total amount of each transition metal in said continuous phase is less than or equal to about 2 ppm.

4. The polymer polyol of claim 1 wherein said polymer polyol contains in excess of 10 ppm transition metal content and at least about 75% of said transition metal content is associated with said dispersed vinyl polymer solids phase.

5. The polymer polyol of claim 1 wherein said polymer polyol contains in excess of 20 ppm transition metal content, the continuous phase containing not more than about 4 ppm transition metal.

6. The polymer polyol of claim 1 wherein said vinyl polymer solid dispersed phase constitutes from about 20 weight percent to about 60 weight percent vinyl polymer solids comprising polymerized acrylonitrile and/or styrene, and wherein said transition metals comprise zinc and cobalt.

7. The polymer polyol of claim 6 wherein the hydroxyl number of said polymer polyol is from about 5 to 70 and wherein the average nominal hydroxyl functionality of said polymer polyol is from about 2 to about 8.

8. The polymer polyol of claim 1 wherein said oxypropylene moiety-containing polyether polyol is a polyether polyol comprising oxypropylene and oxyethylene moieties.

9. A polymer-modified polyol prepared by the in situ polymerization of one or more di- or polyisocyanates with one or more isocyanate-reactive monomers in a base polyol comprising an encapsulative double metal cyanide complex-catalyzed oxypropylene moiety-containing polyoxyalkylene polyether polyol, said polymer-modified polyol having a continuous phase containing said double metal cyanide complex-catalyzed polyether polyol and a dispersed phase containing particles comprising an addition polymerization product of said one or more di- or polyisocyanates and said one or more isocyanate reactive monomers, said polymer-modified polyol containing about 4 ppm or more of transition metals derived from said double metal cyanide complex catalyst, at least about 60% of said transition metals associated with said dispersed phase particles.

10. The polymer-modified polyol of claim 9 wherein at least one of said one or more isocyanate reactive monomers are selected from the group consisting of amines and alkanolamines.

11. The polymer-modified polyol of claim 10 wherein said amine is selected from the group consisting of hydrazine, alkylenediamines, polyalkylenepolyamines.

12. The polymer-modified polyol of claim 10 wherein said alkanolamine is selected from the group consisting of the mono-, di-, and trialkanolamines having from 2 to 8 carbons in the alkanol residues thereof.

13. The polymer-modified polyol of claim 12 wherein said alkanolamine is selected from the group consisting of diethanolamine and triethanolamine.

14. The polymer-modified polyol of claim 9 wherein said polymer-modified polyol contains in excess of about 5 ppm of transition metals and the total amount of each transition metal in said continuous phase is less than or equal to about 1 ppm.

15. The polymer-modified polyol of claim 9 wherein said polymer-modified polyol contains in excess of about 10 ppm of transition metals and the total amount of each transition metal in said continuous phase is less than or equal to about 2 ppm.

16. The polymer-modified polyol of claim 9 wherein said polymer-modified polyol contains in excess of 10 ppm transition metal content and at least about 75% of said transition metal content is associated with said dispersed polymer solids phase.

17. The polymer-modified polyol of claim 9 wherein said polymer-modified polyol contains in excess of 20 ppm transition metal content, the continuous phase containing not more than about 4 ppm transition metal.

18. The polymer-modified polyol of claim 9 wherein said oxypropylene moiety-containing polyether polyol is a polyether polyol comprising oxypropylene and oxyethylene moieties.

\* \* \* \* \*